(12) United States Patent
Irie et al.

(10) Patent No.: US 6,890,305 B2
(45) Date of Patent: May 10, 2005

(54) REAGENT AND METHOD FOR MEASURING LUNG FUNCTION

(75) Inventors: Yasuo Irie, Reading, MA (US); Anil S. Modak, Methuen, MA (US)

(73) Assignee: Cambridge Isotope Laboratories, Andover, MA (US)

( * ) Notice: Subject to any disclaimer, the term of this patent is extended or adjusted under 35 U.S.C. 154(b) by 65 days.

(21) Appl. No.: 10/372,982

(22) Filed: Feb. 26, 2003

(65) Prior Publication Data

US 2003/0171687 A1 Sep. 11, 2003

Related U.S. Application Data

(60) Provisional application No. 60/359,862, filed on Feb. 27, 2002.

(51) Int. Cl.$^7$ ................................................. A61B 5/00
(52) U.S. Cl. .......................... 600/532; 73/23.3; 422/84
(58) Field of Search .......................... 600/532; 73/23.3; 422/84

(56) References Cited

U.S. PATENT DOCUMENTS

| | | | |
|---|---|---|---|
| 5,386,832 A | 2/1995 | Wagner et al. ............... | 128/665 |
| 5,848,975 A | * 12/1998 | Phillips ....................... | 600/532 |
| 5,962,335 A | * 10/1999 | Katzman ..................... | 436/181 |
| 6,312,390 B1 | * 11/2001 | Phillips ....................... | 600/532 |
| 6,726,327 B2 | * 4/2004 | Torrey et al. ................ | 351/243 |

FOREIGN PATENT DOCUMENTS

| | | | | |
|---|---|---|---|---|
| EP | 0966975 A2 | 12/1999 | ......... | A61K/51/08 |
| WO | WO 00/41623 | 7/2000 | ............ | A61B/5/08 |
| WO | WO 01/87352 A1 | 11/2001 | ......... | A61K/51/00 |

OTHER PUBLICATIONS

Schoeller et al, Clinical diagnosis with stable isotope 13C in CO2 breath tests: methodology and fundamental considerations, Journal of Laboratory and Clinical Medicine 1977, 90/3 (412–421).*

Meineke et al, "Evaluation of the 13CO2 kinetics in humans afterioral application of sodium bicarbonate as a model for rbeath testing," EuropeanJournal of Clinical Investigation, (1993) 23, pp. 91–96.*

International Search Report mailed Jul. 21, 2003 from the International Searching Authority.

Kikuchi H. et al. "Influence on diagnosis of Helicobacter pylroi infection in 13C urea breath test of existence of dead space gas." *Sangyo Eiseigaku Zasshi* 41(6):183–89 (Nov. 1999) (Abstract only).

Kikuchi H. et al. "Influence on diagnosis of Helicobacter pylori infection in 13C urea breath test of existence of dead space gas!" Database Medline Online, U.S. National Library of Medicine (NLM), Bethesda, MD, US; Nov. 1999, Database accession No. NLM10637943 XP002246487.

(Continued)

*Primary Examiner*—Robert L. Nasser
(74) *Attorney, Agent, or Firm*—Finnegan, Henderson, Farabow, Garrett, & Dunner, L.L.P.

(57) ABSTRACT

The present invention relates to an assay for evaluating alveolar exchange of oxygen. A $^{13}$C-labeled substrate, such as $^{13}$C-sodium bicarbonate is administered to a subject by oral or iv intake, and exhaled $^{13}CO_2$ is measured. The $^{13}CO_2$ in expired breath can be collected at various time points following administration of the substrate and measured in Δ per mil with a mass analyzer or photometer, such as an IR spectrometer. This process can be used as a diagnostic test for the indication of, treatment and/or evaluation of the severity of respiratory tract diseases or infections.

25 Claims, 4 Drawing Sheets

OTHER PUBLICATIONS

Meineke et al., "Evaluation of the $^{13}CO_2$ Kinetics in Humans after Oral Application of Sodium Bicarbonate as a Model for Breath Testing", *European Journal of Clinical Investigation*, No. 23, 1993, pp. 91–96.

Thangham et al., "Oral Versus Intravenous Administration of $^{13}$C–Bicarbonate", *Med. Sci. Res.*, No. 25, 1997, pp. 9–10.

Horswill et al., "Measuring Energy Costs of Leisure Activity in Adolescents using a $CO_2$ Breath Test", *Medicine & Science in Sports & Exercise*, The American College of Sports Medicine, pp. 1263–1268, 1997.

Gresham et al., "Gastrointestinal Tract, Hepatic, Hindlimb and Renal Recovery of $CO_2$ in vivo", *J. Appl. Physiol.*, vol. 89, 2000, pp. 2000–2006.

Kubo et al., "Non–invasive Approach for Diagnosing Atrophic Gastritis Using the $^{13}$C–bicarbonate Breath Test", *International Journal of Molecular Medicine*, vol. 7, 2001, pp. 381–384.

Shew et al., "Validation of a [13C] Bicarbonate Tracer Technique to Measure Neonatal Energy Expenditure", *Pediatric Research*, vol. 47, No. 6, 2000, pp. 787–791.

Moayyedi, "The Serum $^{13}$C–Bicarbonate Assay: A Replacement for Urea Breath Tests?", *Helicobacter*, vol. 3, No. 1, 1998, pp. 64–65.

Soma et al., "Continuous Estimation of $CO_2$ production during Exercise", *Meth. Inform. Med.*, vol. 36, 1997, pp. 368–371.

Reaich et al., "Recovery of $^{13}$C in breath from infused $NaH^{13}CO_3$ Increases During Euglycaemic Hyperinsulinaemia", *Clinical Science*, vol. 87, 1994, pp. 415–419.

Bjorkman et al., "$^{13}$C–Bicarbonate Breath Test as a Measure of Gastric Emptying", *The American Journal of Gastroenterology*, vol. 86, No. 7, 1991, pp. 821–823.

Bennett et al., "Measurement of ($C^{13}$) Arginine Incorporation into Apolipoprotein B–100 in Very Low Density Lipoproteins and Low Density Lipoproteins in Normal Subjects Using ($^{13}$C)Sodium Bicarbonate Infusion and Isotope Ratio Mass Spectrometry", *Biomedical and Environmental Mass Spectrometry*, vol. 19, 1990, pp. 459–464.

Bresson et al., "Recovery of [$^{13}$C]–bicarbonate as Resiratory $^{13}CO_2$ on Parenterally Fed Infants", *European Journal of Clinical Nutrition*, vol. 44, 1990, pp. 3–9.

Irving et al., "Characterization of $HCO_3/CO_2$ Pool Sizes and Kinetics in Infants", *Pediatric Research*, vol. 19, No. 4, 1985, pp. 358–362.

Hoerr, et al., "Recovery of $^{13}$C in Breath from $NaH^{13}CO_3$ Infused by Gut and Vein: Effect of Feeding", *American Physiological Society*, 1989, pp. E426–E438.

Coleman, et al., "Demystifying Acid–Base Regulation", *NetNurseNotes*, http://ww.manaink.com/nurse/acidbase.html., pp. 1–6.

Spector, et al., "Effects of 6 Weeks of Therapy with Oral Doses of ICI 204,219 a Leukotriene $D_4$ Receptor Antagonist, in Subjects with Bronchial Asthma", *Am. J. Respir. Crit. Care Med.*, vol. 150, 1994, pp. 618–623.

Nathan, et al. "Zafirlukast Improves Asthma Symptoms and Quality of Life in Patients with Moderate Reversible Airflow Obstruction", *J. Allergy Clin. Immunol.*, vol. 102, 1998, pp. 935–945.

Fish, et al. "Zafirlukast for Symptomatic Mild–to–Moderate Asthma: A 13–Week Multicenter Study", pp. 675–690.

Richards, et al. "Energy Cost of Activity Assessed by Indirect Calorimetry and a $^{13}CO_2$ Breath Test", *Medicine & Science in Sports & Exercise*, The American College of Sports Medicine, pp. 834–838, 2001.

* cited by examiner

REAGENT AND METHOD FOR MEASURING LUNG FUNCTION

RELATED APPLICATION

This application claims the benefit of priority from U.S. Provisional Application No. 60/359,862, filed Feb. 27, 2002, the disclosure of which is incorporated herein in its entirety.

FIELD OF THE INVENTION

The present invention relates, generally, to a method of evaluating lung function via a breath assay, by determining the relative amount of $^{13}CO_2$ exhaled upon iv or oral administration of a $^{13}C$-labeled substrate, such as sodium bicarbonate. This process can be used as a diagnostic assay for the treatment and evaluation of respiratory tract diseases or infections and their severity.

BACKGROUND

Over 40 million individuals in the U.S. suffer from any one of the following respiratory tract diseases or infections: chronic obstructive pulmonary disease (COPD), asthma, cystic fibrosis, or other respiratory afflictions. Worldwide, the most serious diseases continue to grow at alarming rates. The prevalence of asthma increased 75% between 1980 and 1995, and an estimated 10% of the population over 64 suffers from COPD. According to statistics from the World Health Organization, COPD is projected to be the 5th leading cause of disease by the year 2020. Americans spend over $6.0 billion/year for treatment of respiratory distress.

There are five main categories of treatment available for COPD:

1. Bronchodilators, such as albuterol, pirbuterol, isoetherine, metaproteranol, terbutaline, salmeterol.
2. Anti-Inflammatories (Steroids), such as prednisone, methylprednisolone.
3. Oxygen
4. Lung Reduction Surgery
5. Transplant Surgery A number of pulmonary function tests (PFT's) are routinely carried out to evaluate the overall performance of lungs. These take from 1-3 hours depending on the tests. These tests include, for example, spirometry, sputum test, lung volume tests, diffusing capacity test, methacholine challenge tests (testing for asthma), allergen bronchial challenge tests (testing for specific allergies), airway resistance test (looking for obstruction in the large airways), and lung compliance test (measuring the elasticity of the lungs, which is reduced in emphysema). X-ray analysis is the diagnostic tool of choice for occupational diseases caused by work environment pollutants, such as, silica, coal, cement, asbestos, smoke, coal dust, etc.

Most of these tests, however, are useful only for evaluating lung capacity, and not lung function. Lung capacity and airway resistance measured by spirometry generally relates to a volume of gas expired by a particular set of lungs. Lung function, in contrast, is the capability of the lung to provide oxygen to the blood and remove carbon dioxide, i.e., the ability to perform alveolar gas exchange efficiently. Any lung obstruction caused by environmental pollutants can affect the extent of alveolar gas exchange, either by slowing down the inhalation of oxygen, the exhalation of carbon dioxide, or both. Lung function, thus, provides a more reliable diagnostic tool for obstructive respiratory problems than lung capacity, as it relates to the efficiency of the gas exchange process.

The only lung function assay available of any clinical significance is Arterial blood gas (ABG). The ABG test produces four main measurements: arterial pH, $paO_2$, $paCO_2$ and $HCO_3^-$. The arterial pH is a measure of the body's acid-base equilibrium. Any major alteration of the pH (normal levels 7.35–7.45) can prove fatal. The arterial $paO_2$ indicates the oxygenation of the blood (normal levels 80–100 mmHg). A low $paO_2$ can also prove fatal and appropriate oxygen therapy is usually given to correct a low $paO_2$. The ability to excrete $CO_2$ is one of the major respiratory functions of the lung, and the arterial $paCO_2$ measures the ability of the body to excrete carbon dioxide (normal levels 35–45 mmHg). An elevated $paCO_2$ may suggest a problem with lung ventilation that could progress to require mechanical ventilation. The importance of bicarbonate ($HCO_3^-$) lies in its role as the renal or metabolic component of acid-base regulation, with normal $HCO_3^-$ levels being 22–28 mEq/L. ABG is, however, an invasive and painful test.

Accordingly, there remains a continuing need to develop an assay to determine lung function.

SUMMARY OF THE INVENTION

One embodiment of the present invention provides a method of evaluating alveolar gas exchange. The method comprises administering a $^{13}C$-labeled substrate to a subject, measuring $^{13}CO_2$ exhaled by the subject, and determining lung function from the measured $^{13}CO_2$.

Another embodiment of the present invention provides a method of treating a respiratory tract disease or infection. The method comprises administering a $^{13}C$-labeled substrate to a subject suspected of having the respiratory tract disease or infection, measuring $^{13}CO_2$ exhaled by the subject, selecting a treatment for the respiratory tract disease or infection, and treating the respiratory tract disease or infection.

Another embodiment of the present invention provides a method of determining the presence of a respiratory tract disease or infection. The method comprises administering a $^{13}C$-labeled substrate to a subject suspected of having the respiratory tract disease or infection, measuring $^{13}CO_2$ exhaled by the subject, and determining lung function from the measured $^{13}CO_2$, wherein the lung function is indicative of the presence of the respiratory tract disease or infection.

Another embodiment of the present invention provides a kit comprising a $^{13}C$-labeled substrate, and instructions provided with the substrate that describe how to determine lung function.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Recently, a number of breath tests using either radioisotope labeled $^{14}$C-sodium bicarbonate or stable isotope labeled $^{13}$C-sodium bicarbonate have been described for evaluating various biological functions such as atrophic gastritis, energy expenditure, *H.pylori* infection, euglycaemic hyperinsulinaemia and gastric emptying. None of these tests, however, has been applied to the diagnostic purpose of indicating the presence of, diagnosing, or stratifying the severity of respiratory tract diseases or infections.

One embodiment of the invention provides a method of evaluating the efficiency of alveolar gas exchange, i.e., gas exchange involving air cells of the lungs, as distinguished from tissue gas exchange. The method generally involves administering a $^{13}$C-labeled substrate to a subject and monitoring the alveolar gas exchange by measuring an exhaled gas, such as $^{13}CO_2$. In one embodiment, the $^{13}$C-labeled substrate can be a carbonate, such as $^{13}$C-sodium bicarbonate. For example, when ingested, a bicarbonate substrate undergoes an acid/base reaction in the gastrointestinal tract and releases $HCO_3^-$. The $HCO_3^-$ is converted to carbon dioxide, which is subsequently released as carbon dioxide from the body by exhalation.

The substrate can be administered non-invasively, such as by oral administration through ingesting a tablet, a powder or granules, a PTP formulation, a capsule, or a solution. Alternatively, the substrate can be administered intravenously.

In one embodiment, the subject is a mammal. In another embodiment, the subject is a human.

In one embodiment, the method comprises measuring the $^{13}CO_2$ exhaled by the subject. The $^{13}CO_2$ can be measured by any method known in the art, such as any method that can detect the amount of exhaled $^{13}CO_2$. For example, $^{13}CO_2$ can be measured spectroscopically, such as by infrared spectroscopy. One exemplary device for measuring $^{13}CO_2$ is the UBiT®-IR300 infrared spectrometer, commercially available from Meretek (Denver, Colo.). The subject, having ingested the $^{13}$C-labeled substrate, can exhale into a breath collection bag, which is then attached to the UBiT®-IR300. The UBiT®-IR300 measures the ratio of $^{13}CO_2$ to $^{12}CO_2$ in the breath. By comparing the results of the measurement with that of a standard, the amount of exhaled $^{13}CO_2$ can be subsequently calculated. Alternatively, the exhaled $^{13}CO_2$ can be measured with a mass analyzer.

In one embodiment, lung function is determined from the measured exhaled $^{13}CO_2$. Lung function can indicate the capability of the lung to efficiently perform cellular respiration. As a result, lung function can provide a reliable property for diagnosing or monitoring respiratory tract diseases or infections.

Figure 3:
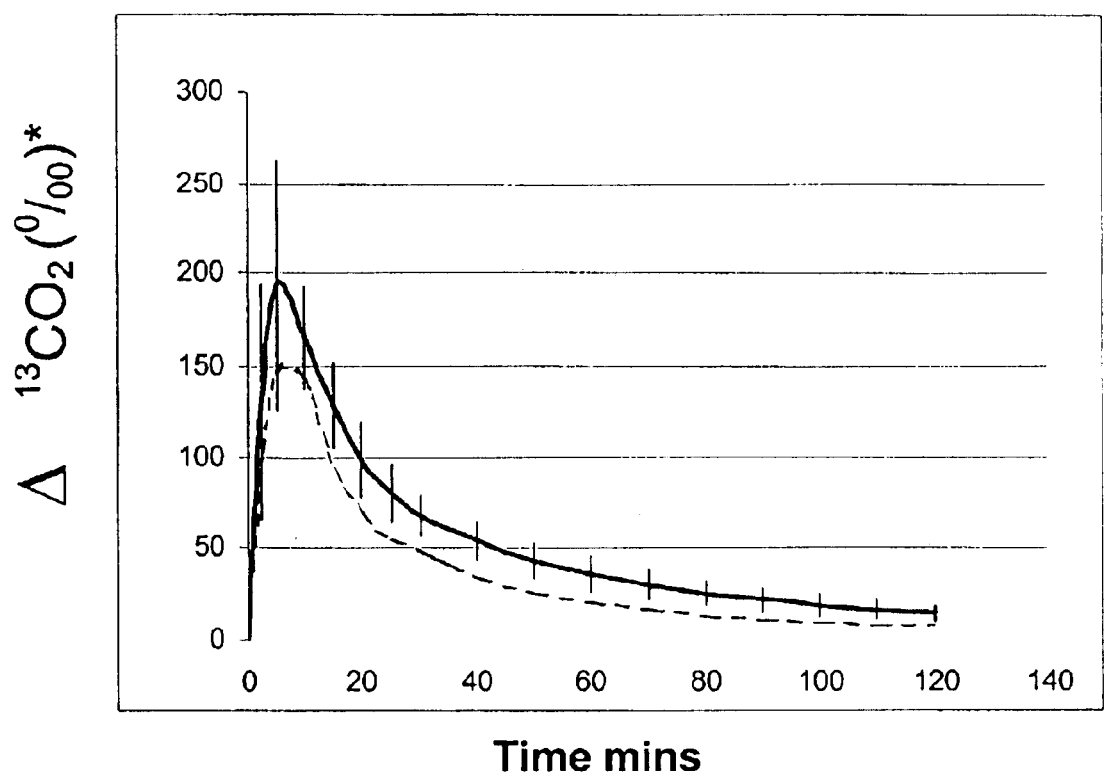
FIG. 3 is a graphical representation of the average of 9 breath curves, with standard deviations, of 6 healthy individuals (solid line) in comparison to a chain smoker (actual data) with an impaired respiratory system (dashed line)

In one embodiment, lung function is determined by an area under the curve (AUC), which plots the amount of exhaled $^{13}CO_2$ on the y-axis versus the time after the $^{13}$C-labeled substrate is ingested. FIG. 3 exemplifies two such breath curves. In FIG. 3, the amount of exhaled $^{13}CO_2$ is quantified as $\Delta\ ^{13}CO_2$ (‰), according to the following equation:

$$\Delta\ ^{13}CO_2(‰)=(\delta\ ^{13}CO_2 \text{ in sample gas})-(\delta\ ^{13}CO_2 \text{ in baseline sample before ingestion})$$

where $\delta$ values are calculated (in ‰) by $=\{(R_{sample}/R_{standard})-1\}\times 1000$, and "R" is the ratio of the heavy to light isotope ($^{13}C/^{12}C$) in the sample or standard. The area under the curve represents the cumulative $\Delta\ ^{13}CO_2$ (‰)×hour.

An individual who develops a respiratory tract disease or infection may show a reduced AUC value compared to a population of healthy individuals (or to another individual given a weight-related dose). Referring to FIG. 3, the top curve represents actual data plotting the average of 9 breath curves of 6 healthy individuals. The bottom curve is that of a chain smoker. It can be seen visually that the AUC for the chain smoker is less than that of the healthy population, indicating that the chain smoker suffers from an impaired respiratory system.

Figure 1:
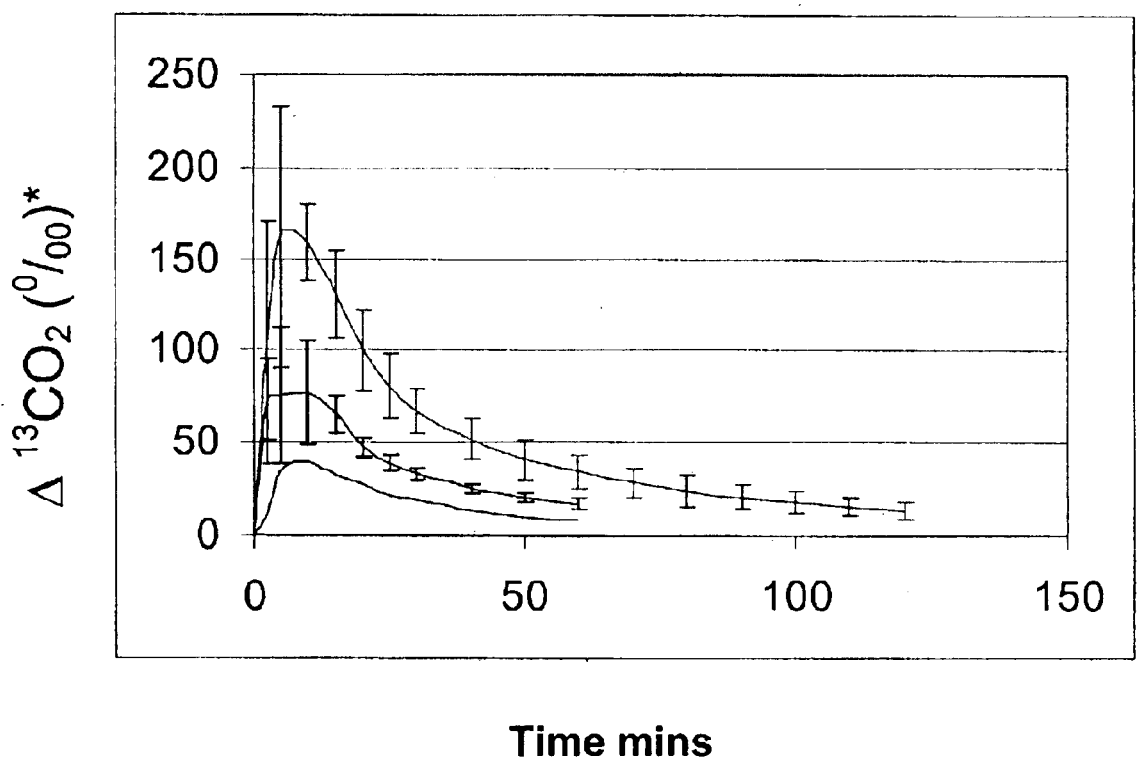
FIG. 1 is a graphical representation of exemplary time and dose responses of expired $^{13}CO_2$ with standard deviations, at $^{13}C$-sodium bicarbonate doses of: 25 mg, n=2 (bottom curve); 50 mg, n=6 (middle curve); 100 mg, n=6 (top curve)
Figure 2:
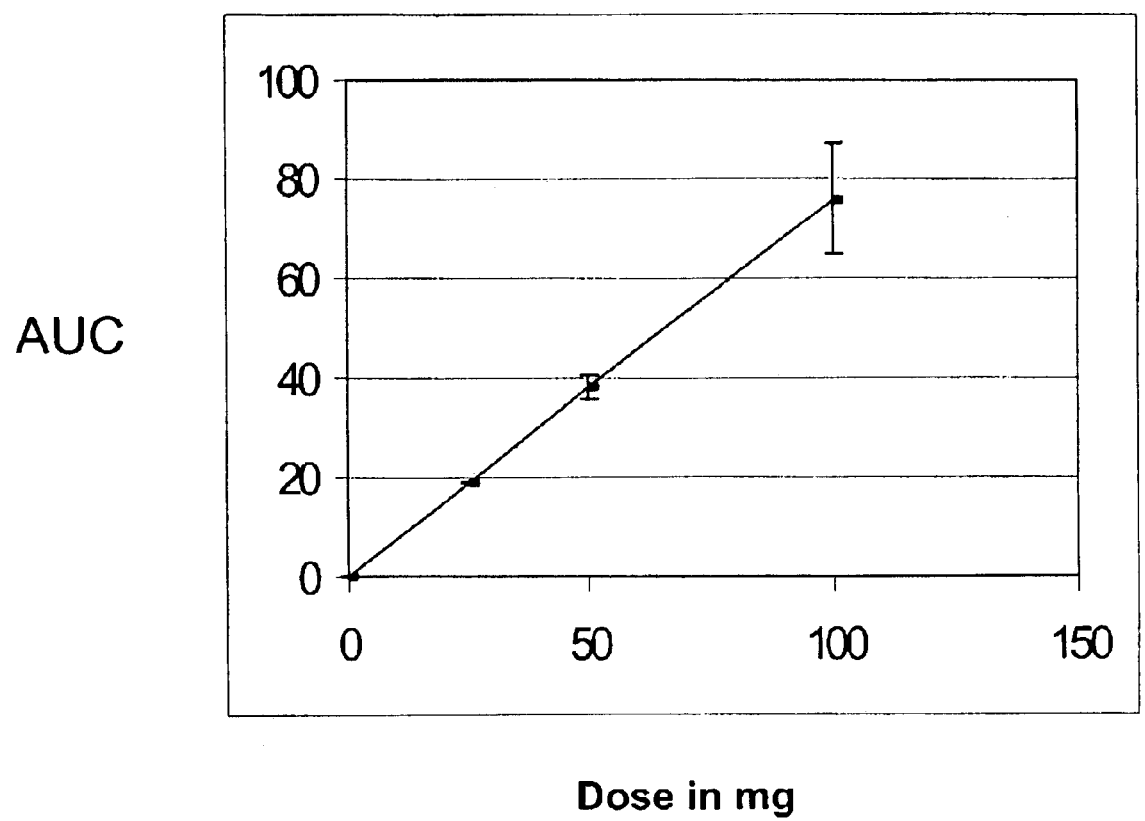
FIG. 2 is a graphical representation of exemplary area under the curve (AUC) values plotted on the y-axis at 25 mg, 50 mg, 100 mg of $^{13}C$-sodium bicarbonate (x-axis)

FIG. 1 shows time and dose response curves for 25 mg (bottom curve), 50 mg (middle curve), and 100 mg (top curve) $^{13}$C-sodium bicarbonate ingested. FIG. 2 shows a plot that visually compares AUC values as a function of the dosage (25 mg, 50 mg, and 100 mg). For an individual, it is understood that a higher dosage of the $^{13}$C-labeled substrate ingested results in a higher AUC.

The method of the invention can be used, for example, as a diagnostic tool. In one embodiment, the AUC curves are compared with those of another individual or a population of individuals. It is generally believed that the amount of exhaled $^{13}CO_2$ is dependent on the body size or weight of the subject. In one embodiment, when comparing AUC values of a patient with another individual, the patient is administered a weight-adjusted dose and compared to another individual who was also administered a weight-adjusted dose. If the patient is compared to a population, the population may be given weight-related doses. In another embodiment, the AUC values are used to monitor an individual's lung function over time. In this embodiment, a weight-related dose is not necessary. Here, the patient can be given any dose, so long as the dosage remains fixed for that individual each time the test is administered.

In another embodiment, lung function can be evaluated by determining the slope of a time and dose response curve where the breath curve exhibits first order decay. In one embodiment, the $\Delta\ ^{13}CO_2$ (‰) values are measured at the following time periods:

$t_0$, the time prior to ingesting the $^{13}$C-labeled substrate;
$t_1$, the time after the $^{13}$C-labeled substrate has been absorbed in the bloodstream of the subject; and
$t_2$, the time during the first elimination phase.

In this embodiment, the slope of the $\Delta\ ^{13}CO_2$ curve at time points $t_1$ and $t_2$ is calculated according to the following equation:

$$\text{slope}=\{(\Delta\ ^{13}CO_2)_2-(\Delta\ ^{13}CO_2)_1\}/(t_2-t_1)$$

Figure 4:
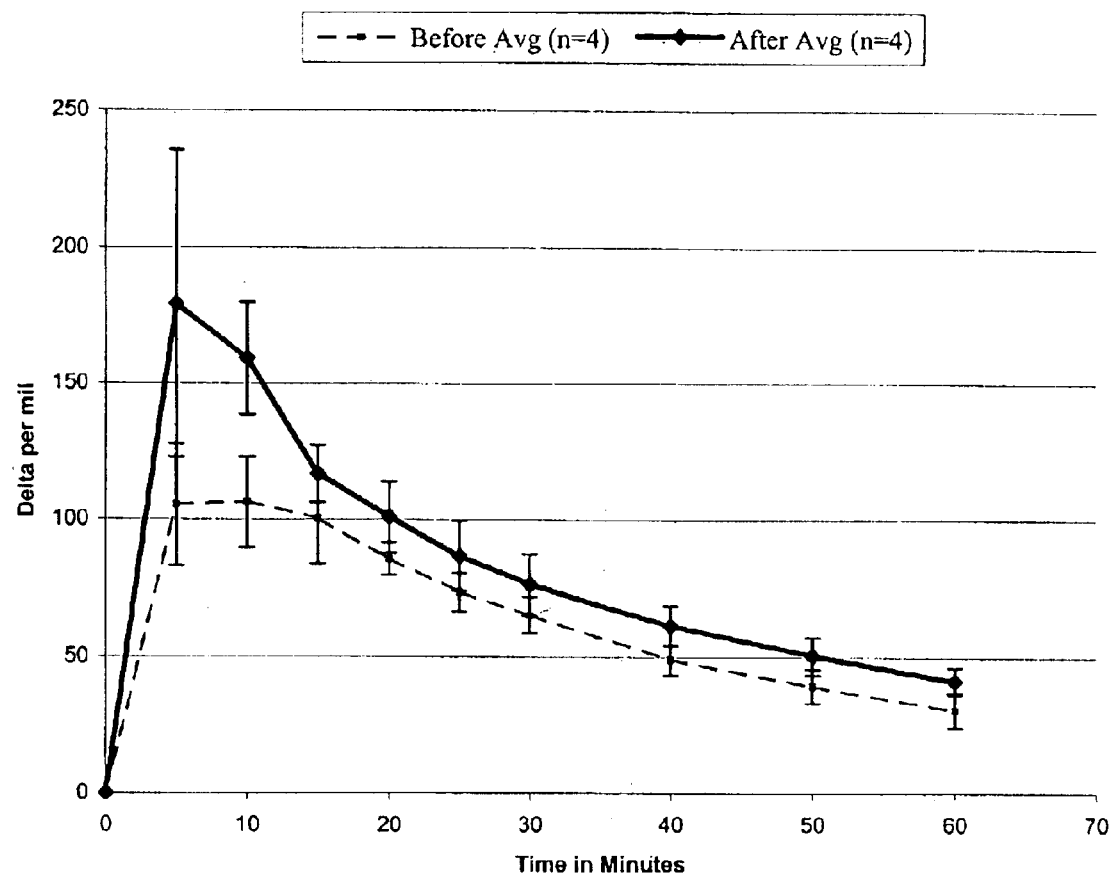
FIG. 4 is a graphical representation of the time and dose response of expired $^{13}CO_2$ pre medication (bottom curve) and post medication (top curve).

As an example, the slope of the curve of FIG. 4 can be measured at the 10 minute time point and the 20 minute time point, to give a variable for determining lung function. FIG. 4 shows dose and time responses for an asthmatic individual before (dashed line) and after (solid line) undertaking inhaler medication therapy. It can be seen from FIG. 4 that the individual post-medication curve has a steeper slope for the 10 and 20 minute time point interval than prior to the medication, indicating an improved lung function. These specific time values are exemplary only and other time periods or half life of the disappearance curve can be used.

In one embodiment, where the slope method is used to determine lung function to compare the lung function of different individuals, the use of weight-adjusted doses is not necessary.

Another embodiment of the present invention provides a method of monitoring treatment, or diagnosing a respiratory tract disease or infection. The method comprises administering a $^{13}$C-labeled substrate to a subject suspected of having the respiratory tract disease or infection, such as any $^{13}$C-labeled substrate described herein. The method further comprises measuring $^{13}CO_2$ exhaled by the subject. In one embodiment, the results of the measured $^{13}CO_2$ can indicate or confirm the presence of at least one respiratory tract disease or infection.

In another embodiment, the invention provides a method of treating a respiratory tract disease or infection. From the results of the measured $^{13}CO_2$, as discussed above, a treatment for the respiratory tract disease or infection can be selected or optimized. The method further comprises treating the respiratory tract disease or infection.

In one embodiment, the treatment is selected from administering a drug, selecting a drug dosage, and oxygen therapy, such as optimized oxygen therapy during the process of weaning a patient from oxygen. For example, depending on the respiratory tract disease or infection, a physician may choose a certain drug to treat the patient. Alternatively, if the patient is already taking a drug, the results of the test may cause a physician to increase or lower the dosage of the drug, depending on the severity of the disease or infection. Another type of treatment is oxygen therapy, where oxygen is administered to a patient to improve the oxygen balance in the blood. In yet another alternative, the results of the test may indicate if the patient should terminate or resume treatment, such as oxygen therapy.

Representative respiratory tract diseases or infections that can be diagnosed or monitored in accordance with the invention include, but are not limited to, chronic obstructive pulmonary disease (COPD), asthma, cystic fibrosis, silicosis, side effects of lung transplantation, bronchitis, bronchiolitis, emphysema caused by alpha 1-antitrypsin deficiency, the common cold, croup, diphtheria, epiglottitis, influenza, lung cancer, measles (rubeola), pertussis (whooping cough), pleurisy, pneumonia, pneumonicosis (such as asbestosis, silicosis, coal workers pneumoconiosis, chronic beryllium disease, and allergic alveolitus), pneumothorax, pulmonary embolism, pulmonary fibrosis, rubella (German measles), rhinitis, sarcoidosis, scarlet fever, sinusitis, sore throat, streptococcal infections, and tuberculosis, and other respiratory afflictions. Thus, this aspect of the invention can be of use to a physician for ascertaining disease status, progression, and drug treatment.

In one embodiment, the measured $^{13}CO_2$ is used to determine lung function. In one embodiment, the lung function can be quantified to determine whether the subject falls above or below a threshold value. This determination can be used to monitor an individual over the course of treatment, where the threshold value is varied for each individual. In one embodiment, the individual is tested at a fixed dosage each time the test is administered. In another embodiment, the threshold value can be determined from a population of individuals tested with a weight-adjusted dose.

In one example, the method can be used for treating and monitoring asthma patients. There are a variety of medications available to relieve respiratory distress (airway passage inflammation). The selection of the proper medication, with a favorable safety profile, can aid in effectively treating asthma patients. Physicians often rely on pulmonary function tests like spirometry—improvements in traditional measures such as FEV1 and PEFR (peak expiratory flow rate)—to help monitor the level of distress in asthma patients. Medications such as corticosteroids (inhaled), Beta 2 Agonists (inhaled) and oral corticosteroids need to be used with utmost caution due to numerous side-effects. The methods described herein can be used to monitor the reduction of airway resistance to individualize medication, e.g., to select and adjust dosage of drugs.

Another embodiment of the invention provides a kit for determining lung function. The kit can include a $^{13}$C-labeled substrate, such as $^{13}$C-sodium bicarbonate, and instructions that describe how to determine lung function. The $^{13}$C-labeled substrate can be supplied as a tablet, a powder or granules, a PTP formulation, a capsule, or a solution. The instructions can describe the method for determining lung function by using the area under the curve, or by the slope technique, as described above.

The kit can optionally include at least three breath collection bags, for measuring the exhaled $^{13}CO_2$ at times $t_0$, $t_1$, and $t_2$. More breath collection bags may be used if additional time periods are necessary. If the $^{13}$C-labeled substrate is supplied as a solid, the kit can also include a container for dissolving the substrate.

In one embodiment, the methods to determine lung function, as described herein, can enable the differentiation of gaseous exchange ($O_2$ and $^{13}CO_2$) between healthy individuals and those with pulmonary disorders. The method can be non-invasive, only requiring that the subject perform a breath test. The present test does not require a highly trained technician to perform the test. The test can be performed at a general practitioners office, where the analytical instrument (such as, for example, a UBiT®-IR300) is installed. Alternatively, the test can be performed at a user's home where the home user can send breath collection bags to a reference lab for analysis. In contrast, the ABG test requires skilled personnel to take arterial blood samples and carry out careful and immediate determination of $pO_2$ and $pCO_2$.

Other embodiments of the invention will be apparent to those skilled in the art from consideration of the specification and practice of the invention disclosed herein. It is intended that the specification and the examples be considered as exemplary only.

EXAMPLE 1

Breath test procedure. Water (100 mL) is added to $^{13}$C-sodium bicarbonate (100 mg) in a 120 mL graduated COrning Snap seal plastic vial (No. 1730-8). The solution is ingested, after overnight fasting, over a time period of approximately 10–15 seconds. Breath samples are collected at 5 minute time points up to 20 minute and then at 30, 40, 50, and 60 minutes after ingestion of $^{13}$C-sodium bicarbonate. The breath samples are collected by momentarily holding the breath for 3 seconds prior to exhaling into the sample collection bag. The breath samples are analyzed on a UBiT IR-300 spectrophotometer sold by Meretek, Denver, Colo., to determine the $^{13}C/^{12}C$ ratio in expired breath, or sent to a reference lab.

EXAMPLE 2

This example describes the monitoring of the reduction in airway resistance in one asthma patient following inhaler medication therapy—advair (fluticasone propionate 100 mcg and salmeterol 50 mcg inhalation powder) and albuterol (racemic ($\alpha^1$-[(tert-butylamino)methyl]-4-hydroxy-m-xylene-$\alpha,\alpha'$-diol, commercially available as Ventolin®, Proventil®) a relatively selective beta$_2$-adrenergic bronchodilator.

A breath test was performed at 7 am before the patient ingested any asthma medication. The medication was taken at 8:15 am. The breath test 45 minutes post medication (9 am) shows an improvement in both the AUC (cumulative‰×h) and possibly the slope (steepening) between 10–20 minutes compared to the pre-medication breath test as seen in FIG. 4.

We claim:

1. A method for evaluating alveolar gas exchange, comprising:

administering a $^{13}$C-labeled substrate to a subject;

measuring $^{13}CO_2$ exhaled by the subject; and determining lung function from the measured $^{13}CO_2$.

2. The method according to claim 1, wherein the $^{13}$C-labeled substrate is a $^{13}$C-labeled carbonate.

3. The method according to claim 2, wherein the $^{13}$C-labeled carbonate is $^{13}$C-sodium bicarbonate.

4. The method according to claim 1, wherein the $^{13}$C-labeled substrate is administered non-invasively.

5. The method according to claim 1, wherein the $^{13}$C-labeled substrate is administered intravenously.

6. The method according to claim 1, wherein the subject is a human.

7. The method according to claim 1, wherein the exhaled $^{13}CO_2$ is measured spectroscopically.

8. The method according to claim 7, wherein the exhaled $^{13}CO_2$ is measured by infrared spectroscopy.

9. The method according to claim 1, wherein the exhaled $^{13}CO_2$ is measured with a mass analyzer.

10. The method according to claim 1, wherein the exhaled $^{13}CO_2$ is measured over at least three time periods to generate a dose response curve, and the lung function is determined from the area under the curve.

11. The method according to claim 10, wherein the exhaled $^{13}CO_2$ is measured over at least two different dosages of the $^{13}$C-labeled substrate.

12. The method according to claim 1, wherein the exhaled $^{13}CO_2$ is measured during at least the following time points:

$t_0$, a time prior to ingesting the $^{13}$C-labeled substrate;

$t_1$, a time after the $^3$C-labeled substrate has been absorbed in the bloodstream of the subject; and $t_2$, a time during the first elimination phase.

13. The method according to claim 12, wherein the lung function is determined from a slope of $\Delta$ $^{13}CO_2$ at time points $t_1$ and $t_2$ calculated according to the following equation:

$$\text{slope} = \{(\Delta\ ^{13}CO_2)_2 - (\Delta\ ^{13}CO_2)_1\}/(t_2 - t_1)$$

wherein $\Delta$ $^{13}CO_2$ is the amount of exhaled $^{13}CO_2$.

14. A method of diagnosing the severity of a respiratory tract disease or infection, comprising:

administering a $^{13}$C-labeled substrate to a subject suspected of having the respiratory tract disease or infection;

measuring $^{13}CO_2$ exhaled by the subject; and diagnosing the severity of the respiratory tract disease or infection based on the amount of $^{13}CO_2$ exhaled by the subject.

15. The method according to claim 14, wherein after the measuring and prior to the diagnosing, the method further comprises determining lung function from the measured $^{13}CO_2$.

16. The method according to claim 14, wherein the respiratory tract disease or infection is selected from chronic obstructive pulmonary disease, asthma, cystic fibrosis, silicosis, side effects of lung transplantation, bronchitis, bronchiolitis, emphysema caused by alpha 1-antitrypsin deficiency, the common cold, croup, diphtheria, epiglottitis, influenza, lung cancer, measles, pertussis, pleurisy, pneumonia, pneumonicosis, pneumothorax, pulmonary embolism, pulmonary fibrosis, rubella, rhinitis, sarcoidosis, scarlet fever, sinusitis, sore throat, streptococcal infections, and tuberculosis.

17. The method according to claim 16, wherein the respiratory tract disease or infection is asthma.

18. The method according to claim 14, wherein the subject is a human.

19. A method of determining the presence of a respiratory tract disease or infection, comprising:

administering a $^{13}$C-labeled substrate to a subject suspected of having the respiratory tract disease or infection;

measuring $^{13}CO_2$ exhaled by the subject; and determining lung function from the measured $^{13}CO_2$;

wherein the lung function is indicative of the presence of the respiratory tract disease or infection.

20. The method according to claim 19, further comprising comparing the lung function to a threshold value.

21. The method according to claim 20, wherein the presence of the respiratory tract disease or infection is indicated if the lung function is below the threshold value.

22. The method according to claim 19, wherein the respiratory tract disease or infection is selected from chronic obstructive pulmonary disease, asthma, cystic fibrosis, silicosis, side effects of lung transplantation, bronchitis, bronchiolitis, emphysema caused by alpha 1-antitrypsin deficiency, the common cold, croup, diphtheria, epiglottitis, influenza, lung cancer, measles, pertussis, pleurisy, pneumonia, pneumonicosis, pneumothorax, pulmonary embolism, pulmonary fibrosis, rubella, rhinitis, sarcoidosis, scarlet fever, sinusitis, sore throat, streptococcal infections, and tuberculosis.

23. The method according to claim 19, wherein the subject is a human.

24. A method of detecting a respiratory tract disease or infection or the severity of a respiratory tract disease or infection, comprising:

administering a $^{13}$C-labeled substrate to a subject suspected of having the respiratory tract disease or infection;

measuring $^{13}CO_2$ exhaled by the subject; and detecting the respiratory tract disease or infection or the severity of a respiratory tract disease or infection based on the amount of $^{13}CO_2$ exhaled by the subject.

25. A method of monitoring the severity of a respiratory tract disease or infection, comprising:

administering a $^{13}$C-labeled substrate to a subject suspected of having the respiratory tract disease or infection;

measuring $^{13}CO_2$ exhaled by the subject at first and second points in time;

determining the severity of the respiratory tract disease or infection based on the amount of $^{13}CO_2$ exhaled by the subject at said first point and second in time;

determining the severity of the respiratory tract disease or infection based on the amount of $^{13}CO_2$ exhaled by the subject at a second point in time.

* * * * *

UNITED STATES PATENT AND TRADEMARK OFFICE
CERTIFICATE OF CORRECTION

PATENT NO. : 6,890,305 B2
DATED : May 10, 2005
INVENTOR(S) : Yasuo Irie and Anil S. Modak It is certified that error appears in the above-identified patent and that said Letters Patent is hereby corrected as shown below:

Column 7,
Line 39, "$^3$C-labeled" should read -- $^{13}$C-labeled --.

Signed and Sealed this

Twelfth Day of July, 2005

JON W. DUDAS
*Director of the United States Patent and Trademark Office*